(12) United States Patent
Barnes

(10) Patent No.: US 11,571,330 B2
(45) Date of Patent: Feb. 7, 2023

(54) AT-HOME CRYOLIPOLYSIS DEVICE AND METHOD OF PERFORMING CRYOLIPOLYSIS

(71) Applicant: Sidney Barnes, Berlin, MD (US)

(72) Inventor: Sidney Barnes, Berlin, MD (US)

( * ) Notice: Subject to any disclaimer, the term of this patent is extended or adjusted under 35 U.S.C. 154(b) by 1083 days.

(21) Appl. No.: 16/205,723

(22) Filed: Nov. 30, 2018

(65) Prior Publication Data

US 2019/0167471 A1 Jun. 6, 2019

Related U.S. Application Data

(60) Provisional application No. 62/594,189, filed on Dec. 4, 2017.

(51) Int. Cl.
*A61F 7/02* (2006.01)
*A61F 7/10* (2006.01)

(52) U.S. Cl.
CPC .............. *A61F 7/02* (2013.01); *A61F 7/10* (2013.01); *A61F 2007/023* (2013.01); *A61F 2007/029* (2013.01); *A61F 2007/0239* (2013.01); *A61F 2007/108* (2013.01)

(58) Field of Classification Search
CPC ............ A61F 2007/0239; A61F 2007/029
See application file for complete search history.

(56) References Cited

U.S. PATENT DOCUMENTS

| 10,206,811 | B2* | 2/2019 | Swyer | A61H 9/0057 |
| 2013/0013037 | A1* | 1/2013 | Adams | A61F 7/0053 |
| | | | | 607/114 |
| 2013/0317578 | A1* | 11/2013 | Diller | A61B 5/01 |
| | | | | 607/104 |
| 2015/0272775 | A1* | 10/2015 | Chehab | A61F 7/10 |
| | | | | 607/114 |

FOREIGN PATENT DOCUMENTS

| EP | 3228285 A1 * | 10/2017 |
| KR | 20150047655 A1 * | 6/2015 |

OTHER PUBLICATIONS

See attached machine translation of KR 20150047655 A1 (Year: 2015).*

* cited by examiner

*Primary Examiner* — Kaitlyn E Smith
(74) *Attorney, Agent, or Firm* — Renner, Otto, Boisselle & Sklar, LLP

(57) ABSTRACT

A cryolipolysis device is provided. The cryolipolysis device includes a suction unit including a flange configured to press against a treatment area of a user, and a chamber contiguous with the flange that defines a cavity configured to receive an ice pack. The cryolipolysis device also includes a manual vacuum device configured to produce suction within the chamber of the suction unit to generate a vacuum to maintain the flange against the treatment area of the user.

6 Claims, 3 Drawing Sheets

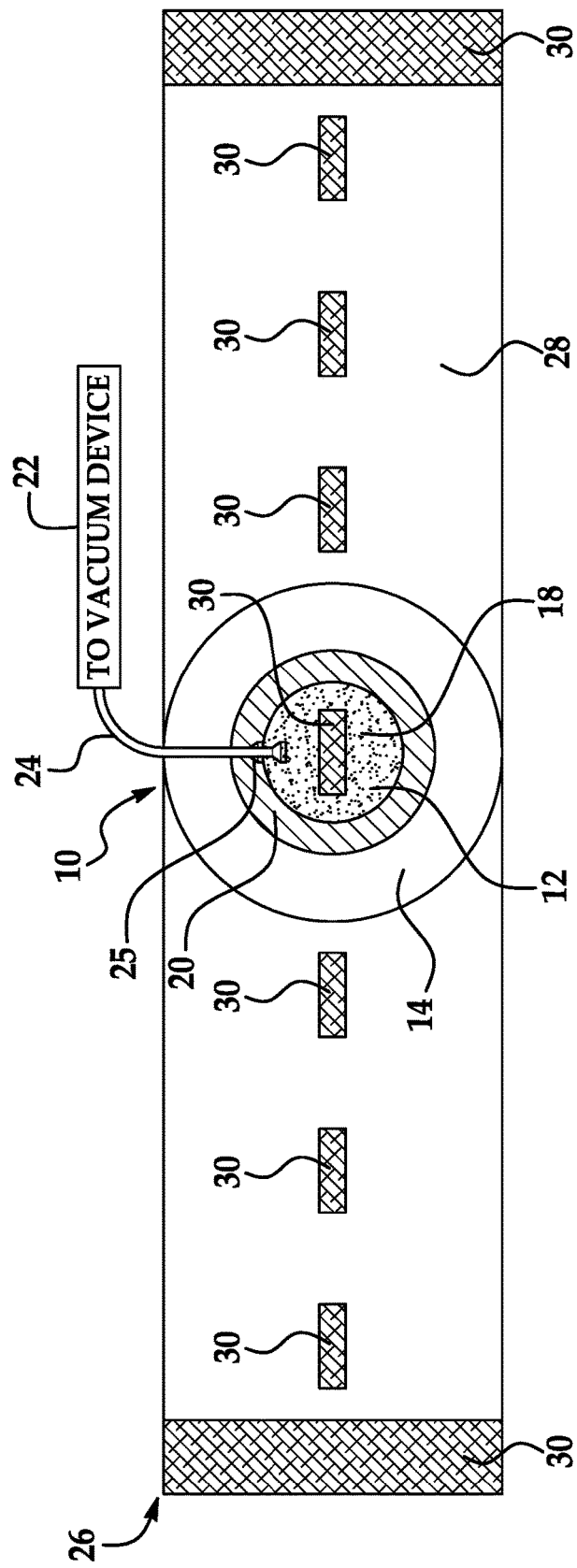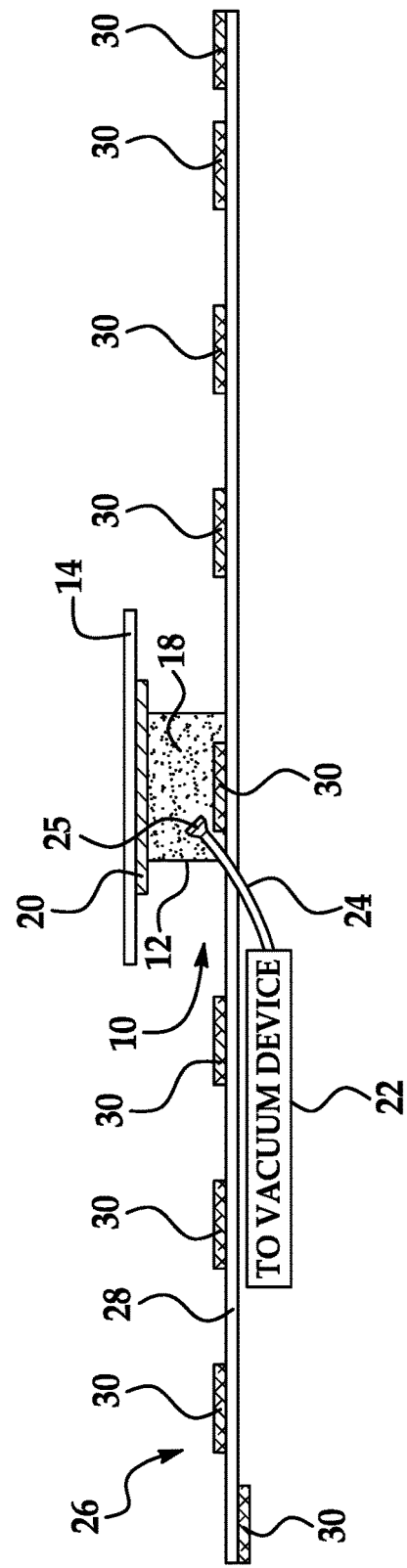
FIG. 3A
FIG. 3B

AT-HOME CRYOLIPOLYSIS DEVICE AND METHOD OF PERFORMING CRYOLIPOLYSIS

PRIOR APPLICATION DATA

This application claims the benefit of the filing date of U.S. Provisional Patent Application No. 62/594,189 filed on Dec. 4, 2017, which is incorporated in its entirety herein by reference.

FIELD OF INVENTION

The present invention relates generally to cryolipolysis, and more particularly to a device and method of performing cryolipolysis at home.

BACKGROUND OF THE INVENTION

Cryolipolysis is the process of destroying fat cells in the subcutaneous tissues using cold temperatures applied to the surface of the skin at a treatment area. Human skin includes a vast plexus of blood vessels which provides the skin with oxygen and nutrients and allows the skin to rapidly heal itself after injury. In subcutaneous tissues, however, blood vessels are sparse. Therefore, subcutaneous tissues are not as easily able to recover from injury as the skin. Accordingly, as an alternative to more invasive treatments for removal of fat cells, cold temperatures have been used to destroy fat cells in the subcutaneous tissues, while sparing the skin.

Current cryolipolysis treatment techniques use temperatures in the range of −5° C. to 5° C., which are effective to destroy fat cells in subcutaneous tissues without damaging skin cells. When applied for about 45 to 60 minutes, this temperature range will cause fat cell death, an inflammatory response, and finally engulfment of the subcutaneous tissue cells by macrophages. This process of cell death, engulfment, remodeling and maturation occurs over the course of several weeks. Complete cryolipolysis treatment typically requires repeated application of these cold temperatures for 45 to 60 minutes to obtain the desired effects. After two to three months of treatment, fat volume in subcutaneous tissues may decrease by up to 25% in the treated area.

Cryolipolysis is typically administered by physicians or suitably trained clinicians at medical facilities or by aestheticians at spas, and in many cases requires the patient to schedule an appointment and travel to the respective location for each treatment. Conventional cryolipolysis machines may include a vacuum to pull tissue into a cup with two panels inside that apply the appropriate temperature to cause cryolipolysis. Cryolipolysis machines such as these may be very costly, costing as much as $3,900. Furthermore, complete cryolipolysis treatment typically involves high cost to the patient, as each treatment application may cost up to $1,500.

SUMMARY OF THE INVENTION

The present invention provides an at-home cryolipolysis device that may be used repeatedly by a consumer, efficiently and conveniently at home, for a fraction of the cost of conventional cryolipolysis treatment. Using appropriate temperature, time and suction, the at-home cryolipolysis device of the present invention is effective to perform cryolipolysis. The at-home cryolipolysis device of the present invention includes a suction cup unit having a chamber for receiving an ice pack, and a flange for tight contact with a treatment area on a user's body. When a vacuum is created within the chamber with a manual vacuum device, a re-freezable saline ice pack, received within the chamber, may contact a surface of the treatment area. The saline ice pack may therefore apply a temperature between −6° C. to −11° C. for a 45 to 60 minute treatment period.

Accordingly, the at-home cryolipolysis device includes a chamber defining a cavity for receiving the ice pack. Contiguous with the chamber is a flange configured to press against a treatment area of the user. After inserting the ice pack into the chamber and positioning the suction cup on the treatment area of the user, the user may employ the manual vacuum device to produce suction within the chamber and create a vacuum to maintain the flange against the treatment area of the user. The surface area of the treatment area covered by the chamber may be drawn into the cavity, wherein the ice pack may contact the surface area of the treatment area to perform cryolipolysis. Contact may then be maintained between the ice pack and the surface area of the treatment area for an amount of time suitable to perform cryolipolysis.

According to an aspect of the invention, a cryolipolysis device is provided. The cryolipolysis device includes a suction unit including a flange configured to press against a treatment area of a user and a chamber contiguous with the flange. The chamber defines a cavity configured to receive an ice pack. The chamber and flange may form formed as a unitary structure of a common material rather than as separate components. The cryolipolysis device also includes a manual vacuum device configured to produce suction within the chamber of the suction unit to generate a vacuum to maintain the flange against the treatment area of the user.

According to another aspect of the invention, a method of performing at-home cryolipolysis is provided. The method includes the step of providing a cryolipolysis device including a suction unit. The suction unit includes a flange configured to press against a treatment area of a user, and a chamber contiguous with the flange. The chamber defines a cavity configured to receive an ice pack. The cryolipolysis device also includes a manual vacuum device configured to produce suction within the chamber of the suction unit to generate a vacuum to maintain the flange against the treatment area of a user. The method also includes the steps of inserting an ice pack into the cavity of the suction unit and positioning the suction unit on the treatment area of the user wherein the chamber of the suction unit covers a surface area of the treatment area. The method also includes the step of employing the manual vacuum device, thereby producing suction within the chamber of the suction unit and drawing the surface area of the treatment area covered by the chamber into the cavity, wherein the ice pack contacts the surface area of the treatment area. The method then also includes the step of maintaining contact between the ice pack and the surface area of the treatment area for an amount of time suitable to perform cryolipolysis.

BRIEF DESCRIPTION OF THE DRAWINGS

FIGS. 3A and 3B are schematic diagrams depicting views of an exemplary at-home cryolipolysis device according to an aspect of the invention.

DETAILED DESCRIPTION

Figure 1:
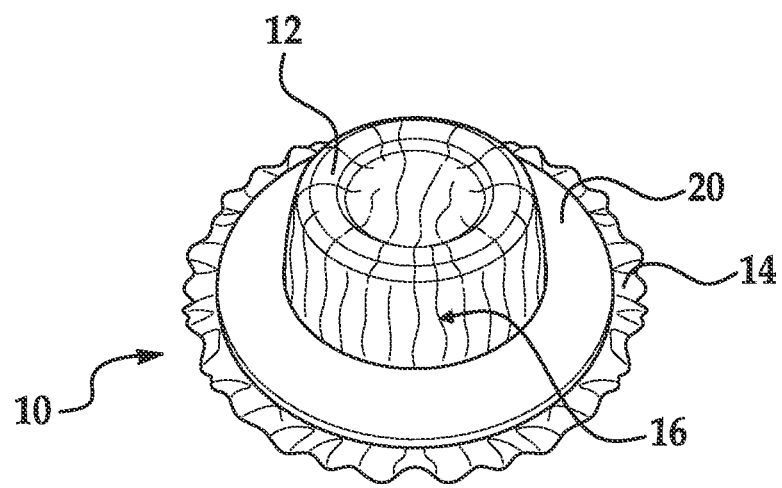
FIG. 1 is a perspective view of an exemplary suction unit used in the at-home cryolipolysis device according to an aspect of the invention.

Embodiments of the present invention will now be described with reference to the drawings, wherein like reference numerals are used to refer to like elements throughout. It will be understood that the figures are not necessarily to scale.

The at-home cryolipolysis device of the present invention can be used repeatedly by a consumer at home efficiently and conveniently, and for a fraction of the cost of conventional cryolipolysis treatment at a typical treatment facility. The at-home cryolipolysis device uses three parameters configured to effectuate cryolipolysis in a treatment area: temperature, time and suction. The at-home cryolipolysis device of the present invention uses a re-freezable saline ice pack to apply a temperature between −6° C. to −11° C. for a 45 to 60 minute treatment period while employing suction to the tissue of a treatment area on a user's body with a manual vacuum creating device.

Figure 4:
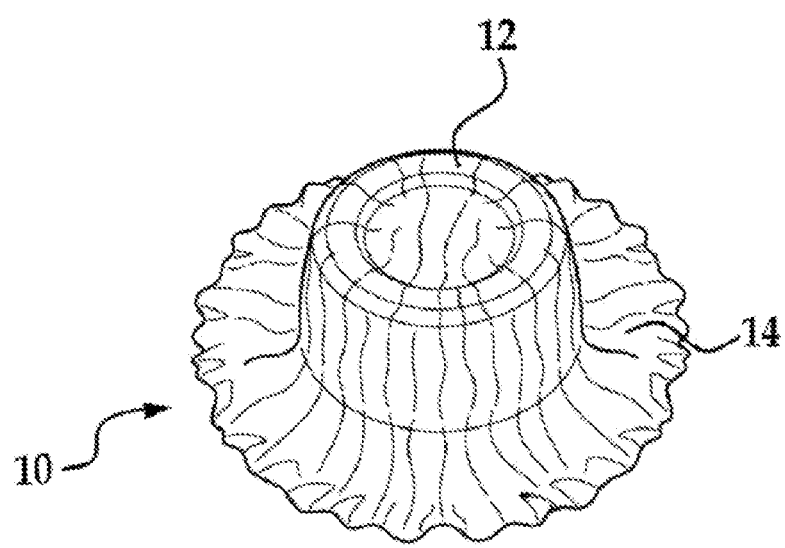
FIG. 4 is a perspective view of another exemplary cryolipolysis device according to an aspect of the invention.

With reference to FIG. 1, the suction unit 10 includes a chamber 12 having a flange 14. The suction unit 10 may be a unitary piece, cast, or otherwise made, from a pliable material such as, for example, silicone. For example, as better depicted in FIG. 4, the chamber 12 and flange 14 of the suction unit 10 may be a unitary structure formed of a common material rather than configured as separate components as shown in FIG. 1. The chamber 12 defines a cavity 16 configured to receive an ice pack 18 that is shown in subsequent figures. The cavity 16 may have a volume of any suitable size for cryolipolysis treatment and is configured to hold the ice pack 18. The chamber 12 may be a bell jar or of any other suitable shape that defines a cavity.

The suction unit 10 may also include a gasket 20 configured to provide structural support to the chamber 12 and flange 14. The gasket 20 may be made of the same material used for the chamber 12 and flange 14, or may be made of a more rigid material such as, for example, plastic or rubber. The gasket 20 may be cast, or otherwise made, with the chamber 12 and flange 14, as a unitary structure, from a pliable material such as, for example, silicone. The gasket 20 may alternatively be separately attached to the chamber 12 and flange 14, specifically being disposed over the flange 14 and around the chamber 12. In an exemplary embodiment, the cavity 16 of the chamber 12 has a diameter of approximately 4.0 inches, the flange 14 has a diameter of approximately 10.0 inches, and the gasket 20 has an outer diameter of approximately 6.0 inches; however, a cavity, flange, and gasket of any suitable size may be used.

Figure 2:
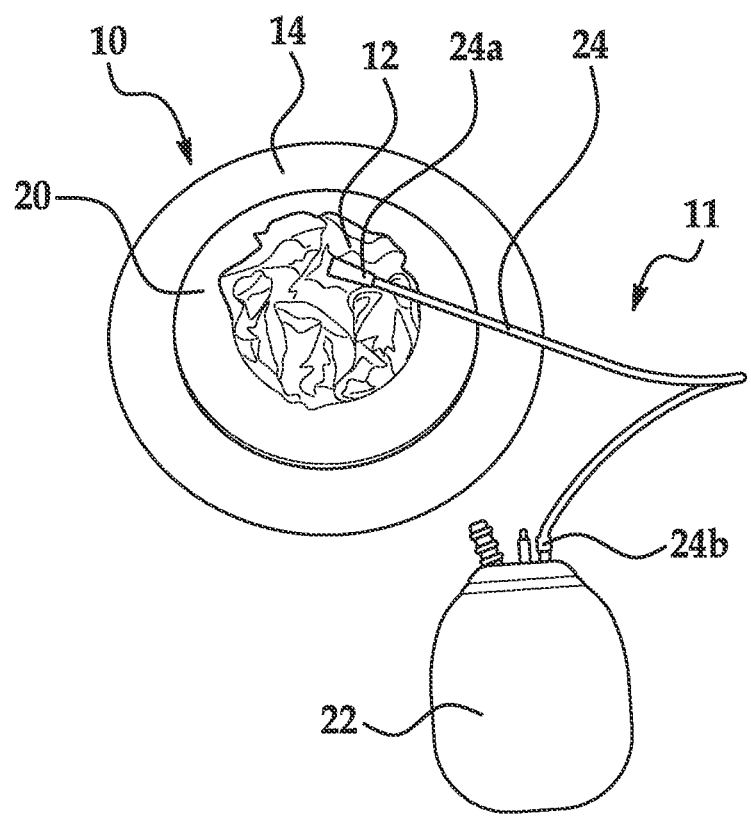
FIG. 2 is a perspective view of an exemplary cryolipolysis device according to an aspect of the invention.

With reference to FIG. 2, the cryolipolysis device 11 may include the suction unit 10 coupled to a vacuum device 22. The vacuum device 22 preferably is manually operated for simple home use as opposed to more complex electronic systems typical of professional cryolipolysis facilities, and is configured to produce suction within the chamber 12 of the suction unit 10. The suction produced by the vacuum device 22 generates a vacuum in the chamber 12 that helps maintain the flange 14 against the skin of a user during treatment. The suction also draws a surface area of the user's skin covered by the chamber 12, referred to herein as the "treatment area", into the cavity 16 for treatment. The suction unit 10 may be coupled to the vacuum device 22 by a tube 24 having a first end 24a coupled to the chamber 12 of the suction unit 10, and a second end 24b coupled to the vacuum device 22. The tube 24 may be made of any suitable material, for example plastic or rubber. The tube 24 may be, for example, a silastic drain or any other tubing material suitable for medical devices. The tube 24 may be coupled to the chamber 12 and the vacuum device 22 with the aid of a grommet 25 or eyelet.

By using a simplified manual vacuum device 22, easy at-home application can be repetitively and conveniently performed by the user. In an exemplary embodiment, the vacuum device 22 is a bulb, such as for example a Jackson-Pratt Drain bulb, that is manually employed by compression. In alternative embodiments, the vacuum device 22 may be any suitable vacuum creating device or suction creating device and may be made of any suitable material, such as for example plastic or rubber. When coupled to the suction unit 10 and employed by the user, the vacuum device 22 is configured to produce around 10 to 20 kPa of suction, or 75 to 600 mmHg, within the chamber 12 of the suction unit 10.

With reference to FIGS. 3A and 3B, various schematic diagrams depicting views of an exemplary at-home cryolipolysis device 26 are shown. The at-home cryolipolysis device 26 uses three parameters configured to effectuate cryolipolysis in a treatment area: temperature, time and suction. While in use, the at-home cryolipolysis device 26 applies a temperature between −6° C. to −11° C. for a 45 to 60 minute treatment period while employing suction to the tissue of a treatment area on the user.

Studies have shown that the mean temperature at the interface between skin and an ice pack made of water, having a melting/freezing point of 0° C., during a 20 minute application of ice was 8.1° C. without compression and 6.1° C. with compression. As these temperatures are outside the appropriate range for cryolipolysis, the ice pack 18 of the at-home cryolipolysis device 26 has a lower melting/freezing point than water. The melting/freezing point of water may be made lower than 0° C. by adding any solute to the water. In an exemplary embodiment, the ice pack 18 includes a saline solution of between 10-15%, having a melting/freezing point of −6° C. to −11° C. As most home freezers are set on average at about −18° C., the ice pack 18 may be conveniently and repetitively frozen in a conventional home freezer.

In an exemplary embodiment, the ice pack 18 is configured to maintain a temperature between −6° C. to −11° C. at the interface between the ice pack 18 and the treatment area of a user for an amount of time suitable to perform cryolipolysis. In this embodiment, the ice pack 18 is configured to maintain a temperature between −6° C. to −11° C. at the interface between the ice pack 18 and the treatment area of a user for a 46 to 60 minute application period. In this embodiment, the ice pack 18 has a volume of 500 ml to one liter of the saline solution, so that the ice pack 18 remains sufficiently small for convenient use, but will remain frozen and maintain a temperature of at least −6° C. to −11° C. at the interface between the ice pack and the treatment area throughout the entire 45 to 60 minute treatment period. Suction is applied to the treatment area via the vacuum device 22 coupled to the suction unit 10 when manually employed by the user, as previously described with reference to FIG. 2.

Additionally, a user of the at-home cryolipolysis device may apply compression during treatment to aid in suction and effectuate a smaller temperature gradient at the interface between the ice pack 18 and the treatment area. Compression may be applied manually or by attaching the at-home cryolipolysis device 11 to a belt 28 configured to wrap around a user's body and compress the suction unit 10 to the treatment area of a user during treatment. The belt 28 may be made of neoprene, or any other suitable flexible and stretchy material. The belt 28 may be made to be any length capable of wrapping around a user's body, and may be made to be a width of at least a diameter of the suction unit 10 of the at-home cryolipolysis device. For example, the belt 28 may be approximately 44.0 inches long and approximately 10.0 inches wide. The belt 28 may include a plurality of attachment members 30 for securing the belt 28 around a user's body. The plurality of attachment members 30 may include any suitable attachment means, such as for example, Velcro, buttons, zippers or the like. The plurality of attachment members may also be positioned along a length of the belt 28 and on the suction unit 10 for attaching the suction unit 10 to the belt 28. Having a plurality of attachment members along the length of the belt 28 and on the suction unit 10 allows the user to move the suction unit 10 to a variety of locations along the belt 28, according to the desired treatment area or to position the suction unit at multiple treatment areas in succession.

A method of using the at-home cryolipolysis device 26 includes positioning the suction unit 10 on the treatment area on a user's body, wherein the chamber 12 of the suction unit 10 covers a surface area of the treatment area. Petroleum jelly may be applied between the treatment area and the flange 14 of the suction unit 10 to aid in flush contact and suction when suction may otherwise be poor due to surface features of the skin, such as bumps or hair. The vacuum device 22 may then be manually employed to produce suction within the chamber 12 of the suction unit 10, thereby drawing the surface area of the treatment area covered by the chamber 12 into the cavity 16. The treatment area then is in contact with the ice pack 18 contained within the cavity 16, and a temperature of at least −6° C. to −11° C. is applied by the ice pack 18 to the treatment area and subcutaneous tissues for a treatment period of about 45 to 60 minutes.

The method may include first attaching the suction unit 10 to the belt 28 via the plurality of attachment members 30 on the belt 28 and the suction unit 10. The belt 28 may then be wrapped and fastened around the user's body to apply compression to the suction unit 10 against the treatment area of the user. The method of using the at-home cryolipolysis device 26 may then be performed as previously described.

The at-home cryolipolysis device 26 of the present invention allows a user to easily and repeatedly perform cryolipolysis treatments efficiently and conveniently, and at a fraction of the cost of conventional cryolipolysis treatments. Effectuating appropriate temperature, time, and suction parameters by methods conveniently operable by the user in the comfort of their own home, the at-home cryolipolysis device 26 is capable of reducing fat content in subcutaneous tissues of a treatment area on a user as effectively as complex professional cryolipolysis machines used in medical facilities or spas, while saving the user time and money.

In an aspect of the invention, a cryolipolysis device is provided. The cryolipolysis device includes a suction unit including a flange configured to press against a treatment area of a user, and a chamber contiguous with the flange that defines a cavity configured to receive an ice pack. The cryolipolysis device also includes a manual vacuum device configured to produce suction within the chamber of the suction unit to generate a vacuum to maintain the flange against the treatment area of the user.

In an embodiment, the cryolipolysis device further includes a tube having a first end coupled to the suction unit and a second end coupled to the vacuum device.

In another embodiment, the first end and the second end of the tube are coupled to the suction unit and vacuum device, respectively, with the aid of a grommet.

In another embodiment, the chamber includes a bell jar.

In another embodiment, the vacuum device is configured to produce 10 to 20 kPa of suction within the chamber of the suction unit.

In another embodiment, the vacuum device includes a bulb.

In another embodiment, the cryolipolysis device further includes an ice pack contained within the cavity.

In another embodiment, the ice pack has a volume of 500 ml to one liter.

In another embodiment, the ice pack has a melting/freezing point of −6° C. to −11° C.

In another embodiment, the ice pack includes a saline solution of between 10-15%.

In another embodiment, the flange and the chamber are a unitary structure of a common material.

In another embodiment, the cryolipolysis device further includes a gasket disposed over the flange of the suction unit.

In another embodiment, the flange, the chamber and the gasket are a unitary structure.

In another embodiment, the suction unit includes silicone.

In another embodiment, the cryolipolysis device further includes a belt configured to compress the suction unit to the treatment area of a user.

In another embodiment, the belt is made of neoprene.

In another embodiment, the suction unit includes a first attachment member and the belt includes a plurality of second attachment members, wherein the suction unit is secured to the belt by joining the first attachment member to one of the second attachment members.

In another aspect of the invention, a method of performing at-home cryolipolysis is provided. The method includes the step of providing a cryolipolysis device including a suction unit. The suction unit includes a flange configured to press against a treatment area of a user, and a chamber contiguous with the flange that defines a cavity configured to receive an ice pack. The cryolipolysis device also includes a manual vacuum device configured to produce suction within the chamber of the suction unit to generate a vacuum to maintain the flange against the treatment area of a user. The method also includes the steps of inserting an ice pack into the cavity of the suction unit and positioning the suction unit on the treatment area of the user wherein the chamber of the suction unit covers a surface area of the treatment area. The method also includes the step of employing the manual vacuum device, thereby producing suction within the chamber of the suction unit and drawing the surface area of the treatment area covered by the chamber into the cavity, wherein the ice pack contacts the surface area of the treatment area. The method also then includes the step of maintaining contact between the ice pack and the surface area of the treatment area for an amount of time suitable to perform cryolipolysis.

In an embodiment, contact between the ice pack and the surface area of the treatment area is maintained for 45 to 60 minutes to perform cryolipolysis.

In another embodiment, the suction unit includes a first attachment member, and the step of positioning the suction unit further includes the steps of providing a belt including a plurality of second attachment members, attaching the suction unit to the belt by joining the first attachment member to one of the second attachment members, and wrapping the belt around the user to apply compression to the suction unit against the treatment area of the user.

In another embodiment, the manual vacuum device is configured to produce 10 to 20 kPa of suction within the chamber of the suction unit.

In another embodiment, the ice pack has a volume of 500 ml to one liter.

In another embodiment, the ice pack has a melting/freezing point of −6° C. to −11° C.

In another embodiment, the ice pack includes a saline solution of between 10-15%.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method of performing at-home cryolipolysis comprising the steps of:
   providing a cryolipolysis device including:
   a suction unit including:
   a flange configured to press against a treatment area of a user, and
   a chamber contiguous with the flange that defines a cavity configured to receive an ice pack, and
   a manual vacuum device configured to produce suction within the chamber of the suction unit to generate a vacuum to maintain the flange against the treatment area of the user;
   inserting an ice pack into the cavity of the suction unit;
   positioning the suction unit on the treatment area of the user wherein the chamber of the suction unit covers a surface area of the treatment area;
   employing the manual vacuum device, thereby producing suction within the chamber of the suction unit and drawing the surface area of the treatment area covered by the chamber into the cavity, wherein the ice pack contacts the surface area of the treatment area; and
   maintaining contact between the ice pack and the surface area of the treatment area for an amount of time suitable to perform cryolipolysis.

2. The method of claim 1, wherein contact between the ice pack and the surface area of the treatment area is maintained for 45 to 60 minutes to perform cryolipolysis.

3. The method of claim 1, wherein the suction unit includes a first attachment member, and the step of positioning the suction unit further comprises the steps of:
   providing a belt including a plurality of second attachment members,
   attaching the suction unit to the belt by joining the first attachment member to one of the second attachment members, and
   wrapping the belt around the user to apply compression to the suction unit against the treatment area of the user.

4. The method of claim 1, wherein the manual vacuum device is configured to produce 10 to 20 kPa of suction within the chamber of the suction unit.

5. The method of claim 1, wherein the ice pack has a melting/freezing point of −6° C. to −11° C.

6. The method of claim 1, wherein the ice pack comprises a saline solution of between 10-15%.

* * * * *